United States Patent
Tarro et al.

(10) Patent No.: US 6,884,411 B1
(45) Date of Patent: Apr. 26, 2005

(54) METHOD OF TREATING VIRAL HEPATITIS BY ADMINISTRATION OF LIQUID HUMAN α-INTERFERON

(75) Inventors: Giulio Tarro, Rome (IT); Renzo Brozzo, Rome (IT)

(73) Assignee: Unihart Corporation, Dublin (IE)

( * ) Notice: Subject to any disclaimer, the term of this patent is extended or adjusted under 35 U.S.C. 154(b) by 0 days.

(21) Appl. No.: 09/125,122

(22) PCT Filed: Feb. 27, 1997

(86) PCT No.: PCT/IT97/00040
§ 371 (c)(1),
(2), (4) Date: Jan. 4, 1999

(87) PCT Pub. No.: WO97/31649
PCT Pub. Date: Sep. 4, 1997

(30) Foreign Application Priority Data

Feb. 28, 1996 (IT) .................. RM96A0136
Jun. 14, 1996 (IT) .................. RM96A0427

(51) Int. Cl.$^7$ .................. A61K 38/21; C07K 14/56
(52) U.S. Cl. .................. 424/85.7; 424/85.4; 514/2; 514/12; 530/351
(58) Field of Search .................. 424/85.7, 85.2, 424/85.4, 85.6, 145.1; 514/383, 2, 12; 530/351

(56) References Cited

U.S. PATENT DOCUMENTS

| | | | | |
|---|---|---|---|---|
| 5,824,300 A | * | 10/1998 | Cummins | 424/85.7 |
| 5,849,696 A | * | 12/1998 | Chretien et al. | 514/2 |
| 5,980,884 A | * | 11/1999 | Blatt et al. | 424/85.4 |
| 6,001,799 A | * | 12/1999 | Chretien et al. | 514/2 |
| 6,048,843 A | * | 4/2000 | Toth | 514/50 |

FOREIGN PATENT DOCUMENTS

| | | | |
|---|---|---|---|
| EP | 1005868 | * | 6/2000 |
| WO | 88/03411 | | 5/1988 |

OTHER PUBLICATIONS

Toyoda et al. Retreatment of chronic hepatitis C with interferon. Am J Gastroenterol 89(9): 1453–1457, 1994.*
Di Bisceglie et al. Recombinant interferon alfa therapy for chronic hepatitis C. New England J Med 321:1506–1510, 1989.*
Davis et al. Treatment of chronic hepatitis C with recombinant interferon alfa. New England J Med 321: 1501–1506, 1989.*
Main, J. Future studies of combination therapy for chronic hepatitis C: optimizing response rates for each hepatitis C population. J Hepatology (Suppl) 23(2): 32–36, 1995.*
Marcellin et al. Recombinant human alpha–interferon in patients with chronic non–a, non–b hepatitis: a multicenter randomized controlled trial from France. Hepatology 13: 393–397, 1991.*
Archivum Immunologiae et Therapiae Experimentalis 41(3–4). 1993: 259–265, J.A. Georgiades; "Early changes in the plasma proteins of patients treated with low doses of oral natural human interferon alpha (IFN–alpha)".
Archivum Immunologiae et Therapiae Experimentalis 41(3–4). 1993; 237–240. B. Ratajczak; "Observation of the effect of low oral doses of human leukocytic interferon alpha in children with chronic HBV infection and impaired immune response".
Archivum Immunologiae et Therapiae Experimentalis 44 (5–6); 1996; 359–366.; Zielinska et al: "Comparison of the long–term effects of treatment with oral and parenteral interferon alpha in chronic viral hepatitis patients".

* cited by examiner

*Primary Examiner*—Elizabeth Kemmerer
*Assistant Examiner*—Bridget E. Bunner
(74) *Attorney, Agent, or Firm*—Baker Botts LLP

(57) ABSTRACT

Use of natural human α-interferon for the preparation of a medicament in liquid form to be administered through peroral route at dosages comprised between 100 UI and 500 UI/day, for therapy of viral infections, in particular viral hepatitis, neoplasia and immune diseases in humans and animals.

6 Claims, No Drawings

METHOD OF TREATING VIRAL HEPATITIS BY ADMINISTRATION OF LIQUID HUMAN α-INTERFERON

This application is a United States national stage application based on International Application No. PCT/IT97/00040, filed Feb. 27, 1997, which claims priority to Italian Patent Applications Nos. RM96A000136 filed Feb. 28, 1996 and RM96A000247 filed Jun. 14, 1996.

The invention concerns pharmaceutical compositions for a peroral administration comprising natural human α-interferon isolated from lymphoblastoid or leukocytic cells. In particular compositions are useful for therapy of viral infections, in particular viral hepatitis, neoplasia and immunodeficiency syndromes. The effective doses of interferon are clearly lower than dosages utilized for parenteral administration.

α-,β-,γ-interferons are usually administered by injection and are used for therapy. α-interferon is the most largely utilized interferon (1). In an updated study of medicaments for either acute or chronic viral hepatitis therapy (2), only α-interferon is widely accepted as a single therapeutic agent.

"Viral hepatitis" means at least five different pathologies, having different causative agents and designated hepatitis A, B, C, D, or E.

The therapeutic trend is to treat said pathologies with α-interferon, with dosages according to the kind of hepatitis, to the overall status of the subject and to other variable factors. In general, further to the interferon treatment an almost normalization in clinical and biochemical parameters is achieved for chronic hepatitis (B,C, or D). The effect of interferon on acute hepatitis has not been determined yet, although for hepatitis C, a therapeutic treatment with α-interferon lowers the chronicity of the disease.

Therapeutic cycles consist of alternate day subcutaneous administration of recombinant α-interferon (r α-IFN) at dosages of approximately 5,000,000 UI, that in special cases can be up to 9,000,000 UI/day.

The length of therapeutic cycles is from six months up to one year (nine months average).

In many cases, undesired side effects interfere with the course of therapeutic treatment. In fact some patients, in particular those at an advanced stage of disease or with severe physiologic damage, do not tolerate the therapy and therefore the treatment should be interrupted. Claimed side effects are: fever, nausea, vomiting, tiredness, pain and depression.

Moreover the therapeutic costs are quite relevant due to the high amount of active principle (more than 8,000 new cases each year in Italy and 300,000 world-wide) and to the necessity of hospitalization just in consideration of said side effects further to the parenteral administration (day hospital or outpatient's department).

Finally, as far as chronic active viral hepatitis the only alternative to the interferon treatment is liver transplant.

The clinical trend is to increase the dosage and the length of therapeutic cycle (3), but clinical data show (4): sever side effects; low acceptance by the patient; and high therapeutic costs. Garcia et al. (5) report that the estimate for each cured patient is between 700,000 and 2,000,000 English pounds. Capri S. (6) report that the cost of each interferon treatment is 70,000,000 Lire/subject.

It is therefore evident that the actual composition of interferon for therapeutic treatment of hepatitis is not optimal.

Moreover clinical results show a better therapeutic efficacy in patients which are not the main target for therapy, namely: young subjects, subjects with a disease at an initial stage, subjects infected with genotypic virus types 2 or 3, and subjects having low viremia. In contrast, less therapeutic efficacy can be found in those subjects which really need the therapeutic treatment (subjects less respondent), as subjects affected by an aggressive form (active chronic hepatitis) or by long-term disease. Thus patients that really need an immediate interferon treatment are those that have a lower chance of being treated successfully.

The authors of the instant invention have found a pharmaceutical composition comprising natural human α-interferon from either lymphoblastoid or leukocytic cells to be administered by the peroral route, with dosages clearly lower than those used for parenteral administration. The composition maintains unaltered the chemical-physical, biological and pharmacological characteristics of the active principle, having a therapeutic effect substantially analogous to the compositions of the prior art but overcoming its disadvantages.

The composition is preferably in a liquid form with a concentration of 100 to 500 IU/ml, preferably approximately 150 UI/ml, most preferably in single-dosage units, most preferably of approximately 1 ml.

The composition acts by activating the defense mechanisms against viral infections, tumor growth and by stimulating an immune response.

The utilization of natural interferon was chosen for the better chances of therapeutic success with respect to recombinant interferon, obtained by cloning of a single subtype.

Though leukocytic and lymphoblastoid interferons exert the same therapeutic properties, the former can be advantageously produced. As a matter of fact it is obtainable by stabilized cell lines, without the need of blood donors.

Processes for purifying interferons are known to those skilled in the art, and for example are shown in U.S. Pat. No. 4,732,683; in Cantell K. and Hirvonen S. Texas Reports on Biology and Medicine, Vol. 35, p. 138, 1977; and in Zoon K. C. et al., Science 207, p. 527,1980.

The peroral route is generally much more accepted by subjects, makes easier therapeutic schemes and dosages, lowers to stops the antigenic risk, induces the transmission and amplification signal mechanism, with a therapeutic effect, with dosages 100 times lower than known formulations for parenteral administrations.

The low dosage annuls the risk of toxic effects; allows a better availability of medicine to satisfy an increasing request and a drastic lowering of therapeutic costs.

The preferred formulation in dosage units of small volumes (1 ml) to drink allows an immediate availability of the active principle, a good standard of cleanliness from the single dose primary container; the certainty of the taken dosage; the taking of the active principle to be immediately absorbed by the oro-pharyngeal mucosa, easily preventing the deglutition, an easy and safe way of administration for all patients, as compared to lozenges or tablet formulations that should be kept in the mouth until completely dissolved, with high chances that the formulation will be swallowed.

Moreover the composition of the invention is conveniently used for home therapies or at the work place, as a precautionary measure for the prophylaxis of viral pathologies, and to control chronic diseases which require long (even yearly) and often recurrent therapeutic cycles.

The composition can be used also in association with other drugs to get synergism and optimize therapeutic schemes.

The following clinical studies show the therapeutic effect. A comparison of the electrophoretic protein pattern and of the concentration of IgG, IgA, and IgM, before the beginning of the peroral therapy with natural human α-interferon of hepatitis or other pathologies before and after two weeks of therapeutic treatment, allows predicting semi-quantitatively the subject response.

Subjects which respond to the therapy with 450 UI/day dosages show a decrease of α2- and β-globulins, of IgGs, of the IgG/IgA ration, together with an increase of IgA and IgM concentrations, have a good chance of eliminating the HBVe antigen and to seroconvert, namely to confer a stable remission of the pathology.

On the other hand subjects which respond to the same therapy with a decrease of serum albumin concentration, of IgGs, IgAs, IgMs, together with an increase of α1-globulin fractions, should seroconvert with longer times.

Moreover subjects that respond with an increase of IgGs, of the IgG/IgA ration, together with a decrease of IgM and of the IgA/IgM ratio, could be resistant to the therapy.

The monitoring of said parameters (markers) is useful for a planning of therapeutic strategies in clinic and also for the clinical practitioner.

Clinical studies on healthy subjects.

Table 1 shows different therapeutic schemes.

TABLE 1

| Exp. | | active comp. | No. admin./day | Dosages | days trt. | blood bleedings |
|---|---|---|---|---|---|---|
| A | aA | α-IF | 1 (3 dsg) | 450 UI | 1 | $T_0, T_1, T_2, T_3$ |
| | aB | placebo | 1 (3 dsg) | — | 1 | $T_0, T_1, T_2, T_3$ |
| B | bA | α-IF | 1 (3 dsg) | 450 UI | 5 | $T_0, T_1, T_2, T_3, T_4, T_5, T_6, T_7$ |
| | bB | placebo | 1 (3 dsg) | — | 5 | $T_0, T_1, T_2, T_3, T_4, T_5, T_6, T_7$ |
| C | $cA_1$ | α-IF | 2 (1 dsg) | 300 UI | 1 | $T_0, T_1, T_2, T_3$ |
| | $cA_2$ | α-IF | 3 (1 dsg) | 450 UI | 1 | $T_0, T_1, T_2, T_3$ |
| | cb | placebo | 3 (1 dsg) | — | 1 | $T_0, T_1, T_2, T_3$ |
| D | $dA_1$ | α-IF | 2 (1 dsg) | 300 UI | 5 | $T_0, T_1, T_2, T_3, T_4, T_5, T_6, T_7$ |
| | $dA_2$ | α-IF | 3 (1 dsg) | 450 UI | 5 | $T_0, T_1, T_2, T_3, T_4, T_5, T_6, T_7$ |
| | dB | placebo | 3 (1 dsg) | — | 5 | $T_0, T_1, T_2, T_3, T_4, T_5, T_6, T_7$ | wherein
$T_0$ = background; $T_1$ = 1 d [further] after the first administration, $T_2$ = 2 d [further] after the first administration, $T_3$ = 3 d [further] after the first administration, $T_4$ = 4 d [further] after the first administration, $T_5$ = 5 d [further] after the first administration, $T_6$ = 1 d after the treatment suspension, and $T_7$ = 2 d after the treatment suspension.

The change of the induced biological response with respect to the therapeutic scheme, has been measured on samples of blood, taken at different times. In particular the activity with respect to the day dosage of active principle, to the mono- or pluri-administration, and to the length of the therapeutic cycle was measured.

The analysis of data show that natural human α-interferon from either lymphoblastoid or leukocytic cells, administered at low dosages for a peroral route, is able to modulate (according to the dosage and to the length of the therapeutic cycle) the expression of membrane antigen of healthy subject blood mononuclear cells. In particular, according to the therapeutic scheme, the pharmaceutical composition seems to be able to increase both CD4 and CD8 cell populations. Increased expression of markers of cell activation, such as DR antigens and the interleukin 2 receptor, is also evident.

The therapeutic scheme with 450 U/day×5 d (exp. b) provided better results, as shown in Tables 2 and 3. In fact there is an increase (% and absolute) in CD3, CD4, DR1, and CD25 lymphocytes, said increases are, according to different cases, more evident at $T_3$, $T_4$, and $T_5$ times and later decrease at $T_6$ and $T_7$ times.

The same dosage, but with a shorter therapeutic cycle (1 day) (exp.a), interferes less evidently with the percentage and absolute numbers of mononuclear cells in the blood (Tables 4 and 5). In fact in this experiment an increase of average percentage values but not of absolute T, CD8, and class I histocompatibility antigen lymphocyte values, is evident at time $T_3$ Other experimental conditions show lower increases of the immune response.

Therefore, natural human α-interferon from either lymphoblastoid or leukocytic cells, administered at low dosages via the peroral route, plays an important role in modulating the immune response, both in the afferent and efferent phases and has a therapeutic application for the treatment of infective diseases and of other conditions of immunodeficiency.

Clinical studies on hepatitis subjects.

Viral B Hepatitis 14 patients affected by chronic viral B hepatitis, between 4 and 59 years of age, were used for random studies.

All subjects were previously treated for different periods ranging from some months to some years with steroids or with steroid-azothiopurine, with no beneficial effects, neither for the clinical symptomatology nor for the biochemical parameters of the disease, which evolved, in some cases, to hepatic cirrhosis.

The therapeutic treatment of one administration of 150 U/day was initiated immediately after the suspension of the previous treatment, and effects of said treatment were monitored by checking any alteration of the immune response; of the haematological and biochemical parameters; of serum markers of the viral infection and of the histochemistry of hepatic biopsy samples.

The time of observation varied from 15 to 32 months and the results can be summarized as follows:

1) all patients during the first 3–6 weeks of treatment registered a transient decay of hepatic biochemical functions (i.e. a 2–3 fold increase of alanine aminetransferase (ALT) levels), with no clinical symptoms of disease worsening;
2) the phenomenon continued for 4–6 weeks;
3) in all treated patients an intense activation of the immune response was observed, even after the therapeutic treatment;
4) 7 patients eliminated HBV DNA and HBeAg from their serum and were stably seroconverted;
5) 1 patient had an increased HBeAg titer, more than the original value; and
6) in the other 9 patients said titer decreased significantly.

Therefore, 50% of patients get a stable remission of the disease.

Viral C Hepatitis

The therapeutic standard of viral hepatitis C foresees the use of α-interferon through the parenteral route.

6 active chronic hepatitis C affected patients were subjected to therapy with peroral administration at 150U/day, by starting the treatment just after the suspension of the steroid therapy.

The observation time (equal to the length of the treatment) varied from 19 to 69 weeks. In general the treatment was well tolerated and all of the patients registered a significant increase of vivacity and appetite, with a better tolerance to physical exercises.

No patients got a normalization of transaminase levels during the observation period, but one demonstrated the biochemical and clinical remission of the disease, after the treatment suspension at the 19th week due to an increase in articular pains.

Results are shown in tables 2–5.

BIBLIOGRAPHY

1) Howard M. et al., The Sciences n.311 Vol. LIII 72–80 (1994).
2) Saracco G., Rizzetto M. Biomed. Pharmacother. 49 (2), 55–57 (1995).
3) Kasahara A. K. et al., Hepatology; 21, 291–291 (1995).
4) Paoletti A. et al.; Clin. Ter. 146(5), 343–349 (1995).
5) Garcia De Ancos J. L. et al.; J. Hepatol. 11:s11–s18 (1990).
6) Capri S. Adis International, Milan, pp. 41–49 (1994).
7) Bianchi F. B., La rivista del medico practico (The review of practical medicine), October (suppl. 5) (1995).

TABLE 2

| TREATMENT | | TIME | % CD3 | % CD4 | % CD8 | % CD25 | % MHCH | % B | % NK | % CD14 |
|---|---|---|---|---|---|---|---|---|---|---|
| 450 UI/d × 5 d | 3 ds | $T_0$ | 69.2 ± 4.9 | 42.8 ± 4.3 | 26.3 ± 2.9 | 1.4 ± 0.9 | 7.5 ± 0.8 | 11.5 ± 1.1 | 6.9 ± 0.7 | 10.3 ± 1.6 |
| PLACEBO × 5 d | 3 ds | $T_0$ | 71.3 ± 5.2 | 41.7 ± 4.1 | 24.5 ± 3.5 | <0.5 | 8.1 ± 1.2 | 13.1 ± 1.6 | 8.1 ± 1.3 | 9.3 ± 1.2 |
| 450 UI/d × 5 d | 3 ds | $T_1$ | 70.1 ± 4.1 | 43.1 ± 4.5 | 25.8 ± 3.1 | <0.5 | 8.2 ± 1.3 | 12.1 ± 1.4 | 7.2 ± 1.3 | 3.9 ± 1.4 |
| PLACEBO × 5 d | 3 ds | $T_1$ | 72.4 ± 5.4 | 40.8 ± 3.9 | 25.3 ± 3.8 | <0.5 | 8.7 ± 1.4 | 12.7 ± 1.6 | 8.2 ± 1.5 | 10.1 ± 1.3 |
| 450 UI/d × 5 d | 3 ds | $T_2$ | 70.2 ± 5.1 | 44.2 ± 3.1 | 23.2 ± 3.1 | 1.7 ± 1.3 | 9.1 ± 1.3 | 12.5 ± 1.6 | 7.1 ± 0.9 | 11.1 ± 1.5 |
| PLACEBO × 5 d | 3 ds | $T_2$ | 70.8 ± 5.3 | 41.1 ± 4.2 | 24.7 ± 3.7 | 1.2 ± 0.9 | 8.7 ± 1.4 | 11.4 ± 1.6 | 6.9 ± 1.9 | 10.8 ± 1.7 |
| 450 UI/d × 5 d | 3 ds | $T_3$ | 69.8 ± 5.7 | 49.4 ± 4.9 | 24.1 ± 3.6 | 2.5 ± 1.6 | 14.2 ± 1.3 | 12.1 ± 1.4 | 7.2 ± 1.1 | 9.7 ± 1.8 |
| PLACEBO × 5 d | 3 ds | $T_3$ | 71.3 ± 5.6 | 41.5 ± 4.3 | 24.4 ± 3.5 | <0.5 | 8.5 ± 1.3 | 13.1 ± 1.8 | 6.9 ± 1.7 | 10.1 ± 1.8 |
| 450 UI/d × 5 d | 3 ds | $T_4$ | 72.3 ± 5.8 | 49.7 ± 5.1 | 23.8 ± 3.8 | 2.3 ± 0.7 | 14.2 ± 2.5 | 12.5 ± 1.8 | 6.8 ± 0.9 | 9.4 ± 1.5 |
| PLACEBO × 5 d | 3 ds | $T_4$ | 69.8 ± 5.3 | 40.9 ± 4.2 | 25.2 ± 4.3 | <0.5 | 7.9 ± 0.9 | 12.9 ± 1.9 | 7.1 ± 0.7 | 11.6 ± 2.1 |
| 450 UI/d × 5 d | 3 ds | $T_5$ | 71.8 ± 5.4 | 53.3 ± 4.9 | 74.2 ± 4.1 | 2.5 ± 1.6 | 14.2 ± 1.9 | 13.5 ± 2.1 | 7.3 ± 0.9 | 11.3 ± 1.6 |
| PLACEBO × 5 d | 3 ds | $T_5$ | 70.6 ± 5.5 | 41.3 ± 4.1 | 25.9 ± 4.4 | 1.4 ± 1.3 | 8.1 ± 1.3 | 12.6 ± 1.4 | 7.5 ± 0.9 | 9.9 ± 2.3 |
| 450 UI/d × 5 d | 3 ds | $T_6$ | 69.7 ± 5.2 | 50.7 ± 4.7 | 23.7 ± 4.1 | 1.6 ± 0.9 | 11.3 ± 1.5 | 12.8 ± 1.9 | 6.9 ± 0.6 | 10.8 ± 1.9 |
| PLACEBO × 5 d | 3 ds | $T_6$ | 71.3 ± 5.6 | 42.3 ± 4.3 | 24.7 ± 3.8 | <0.5 | 7.9 ± 1.4 | 11.4 ± 1.1 | 7.3 ± 0.5 | 10.4 ± 1.9 |
| 450 UI/d × 5 d | 3 ds | $T_7$ | 70.2 ± 5.1 | 45.3 ± 4.4 | 24.2 ± 3.8 | 1.1 ± 0.9 | 8.7 ± 1.1 | 12.3 ± 1.6 | 7.1 ± 0.7 | 11.2 ± 7.1 |
| PLACEBO × 5 d | 3 ds | $T_7$ | 71.5 ± 5.8 | 41.5 ± 3.9 | 25.1 ± 4.1 | <0.5 | 8.1 ± 1.6 | 11.9 ± 1.4 | 7.8 ± 0.8 | 9.8 ± 1.7 | b vs a = p < 0.05; c vs a = p < 0.01; e vs d = p < 0.01; f vs d = p < 0.05
Student's "t" test

TABLE 3

| TREATMENT | | TIME | CD3 n°/mm³ | CD4 n°/mm³ | CD8 n°/mm³ | CD25 n°/mm³ | MHCH n°/mm³ | B n°/mm³ | NK n°/mm³ | CD14 n°/mm³ |
|---|---|---|---|---|---|---|---|---|---|---|
| 450 UI/d × 5 d | 3 ds | $T_0$ | 1776 ± 323 | 1074 ± 108 | 560 ± 145 | 35 ± 23 | 188 ± 60 | 288 ± 87 | 173 ± 88 | 177 ± 78 |
| PLACEBO × 5 d | 3 ds | $T_0$ | 1658 ± 320 | 970 ± 195 | 565 ± 171 | <13 | 186 ± 68 | 305 ± 77 | 188 ± 90 | 203 ± 88 |
| 450 UI/d × 5 d | 3 ds | $T_1$ | 1858 ± 128 | 1142 ± 213 | 684 ± 95 | <13 | 217 ± 53 | 320 ± 65 | 191 ± 73 | 213 ± 95 |
| PLACEBO × 5 d | 3 ds | $T_1$ | 1784 ± 195 | 1005 ± 191 | 623 ± 102 | <13 | 214 ± 73 | 313 ± 141 | 302 ± 85 | 216 ± 90 |
| 450 UI/d × 5 d | 3 ds | $T_2$ | 1988 ± 130 | 1251 ± 115 | 657 ± 198 | 48 ± 33 | 258 ± 43 | 354 ± 70 | 301 ± 73 | 196 ± 138 |
| PLACEBO × 5 d | 3 ds | $T_2$ | 1746 ± 183 | 1034 ± 197 | 594 ± 182 | 30 ± 20 | 285 ± 103 | 281 ± 87 | 170 ± 84 | 205 ± 140 |
| 450 UI/d × 5 d | 3 ds | $T_3$ | 1878 ± 132 | 1339 ± 223 | 648 ± 190 | 67 ± 40 | 382 ± 65 | 326 ± 65 | 194 ± 78 | 243 ± 75 |
| PLACEBO × 5 d | 3 ds | $T_3$ | 1555 ± 190 | 905 ± 230 | 530 ± 81 | <11 | 185 ± 130 | 286 ± 52 | 150 ± 99 | 234 ± 72 |
| 450 UI/d × 5 d | 3 ds | $T_4$ | 1994 ± 178 | 1325 ± 168 | 539 ± 195 | 62 ± 43 | 381 ± 90 | 336 ± 145 | 163 ± 75 | 187 ± 48 |
| PLACEBO × 5 d | 3 ds | $T_4$ | 1233 ± 213 | 1138 ± 197 | 701 ± 200 | <14 | 230 ± 121 | 359 ± 174 | 198 ± 76 | 167 ± 69 |
| 450 UI/d × 5 d | 3 ds | $T_5$ | 2001 ± 175 | 1456 ± 283 | 579 ± 203 | 70 ± 40 | 399 ± 108 | 379 ± 88 | 205 ± 73 | 197 ± 140 |
| PLACEBO × 5 d | 3 ds | $T_5$ | 1720 ± 226 | 1007 ± 195 | 531 ± 132 | 34 ± 31 | 197 ± 115 | 307 ± 153 | 183 ± 74 | 196 ± 731 |
| 450 UI/d × 5 d | 3 ds | $T_6$ | 1719 ± 170 | 1238 ± 175 | 585 ± 170 | 39 ± 23 | 375 ± 138 | 316 ± 84 | 170 ± 75 | 213 ± 68 |
| PLACEBO × 5 d | 3 ds | $T_6$ | 1578 ± 230 | 736 ± 300 | 547 ± 138 | <11 | 175 ± 131 | 252 ± 126 | 162 ± 62 | 242 ± 74 |
| 450 UI/d × 5 d | 3 ds | $T_7$ | 1704 ± 128 | 1058 ± 170 | 586 ± 105 | 27 ± 23 | 281 ± 128 | 298 ± 97 | 172 ± 78 | 197 ± 83 |
| PLACEBO × 5 d | 3 ds | $T_7$ | 1595 ± 235 | 974 ± 191 | 559 ± 195 | <11 | 160 ± 51 | 265 ± 133 | 174 ± 65 | 228 ± 90 | b vs s = p < 0.05; d vs c = p < 0.05; f vs c = p < 0.01
Student's "t" test

TABLE 4

| TREATMENT | | TIME | % CD3 | % CD4 | % CD8 | % CD25 | % MHCH | % B | % NK | % CD14 |
|---|---|---|---|---|---|---|---|---|---|---|
| 450 UI/d × 1 d | 3 ds | $T_0$ | 70.3 ± 5.7 | 42.4 ± 3.8 | 25.3 ± 2.6 | 1.7 ± 1.4 | 7.2 ± 0.8 | 9.7 ± 1.4 | 8.4 ± 0.9 | 8.4 ± 0.7 |
| PLACEBO × 1 d | 3 ds | $T_0$ | 69.9 ± 5.3 | 43.8 ± 4.2 | 24.3 ± 2.7 | <0.5 | 7.9 ± 0.9 | 10.9 ± 1.7 | 7.8 ± 0.8 | 9.8 ± 0.89 |
| 450 UI/d × 1 d | 3 ds | $T_1$ | 69.4 ± 5.5 | 43.9 ± 4.5 | 24.8 ± 1.9 | <0.5 | 8.3 ± 1.3 | 10.5 ± 1.7 | 9.3 ± 2.1 | 8.3 ± 0.8 |
| PLACEBO × 1 d | 3 ds | $T_1$ | 70.2 ± 5.9 | 43.5 ± 4.1 | 23.8 ± 2.5 | <0.5 | 8.2 ± 1.3 | 11.2 ± 1.8 | 7.3 ± 2.1 | 8.5 ± 0.6 |
| 450 UI/d × 1 d | 3 ds | $T_2$ | 73.6 ± 6.1 | 43.5 ± 4.3 | 27.3 ± 3.1 | <0.5 | 8.1 ± 1.2 | 11.2 ± 2.1 | 10.7 ± 4.5 | 9.3 ± 1.5 |
| PLACEBO × 1 d | 3 ds | $T_2$ | 70.1 ± 5.6 | 44.1 ± 4.7 | 24.7 ± 3.1 | 1.4 ± 0.8 | 7.7 ± 1.4 | 12.1 ± 2.7 | 8.1 ± 0.9 | 8.8 ± 1.3 |
| 450 UI/d × 1 d | 3 ds | $T_3$ | 77.8 ± 6.2 | 44.1 ± 1.6 | 2.7 ± 2.4 | 2.3 ± 1.9 | 11.2 ± 1.5 | 10.9 ± 1.9 | 8.3 ± 0.7 | 12.2 ± 3.1 |
| PLACEBO × 1 d | 3 ds | $T_3$ | 70.3 ± 5.4 | 43.9 ± 5.1 | 24.7 ± 3.3 | <0.5 | 8.1 ± 0.9 | 10.5 ± 1.7 | 8.5 ± 1.6 | 10.7 ± 1.4 | b vs a = p < 0.01; c vs d = p < 0.05; e vs f = p < 0.05
Student's "t" test

TABLE 5

| TREATMENT | | TIME | CD3 n°/mm³ | CD4 n°/mm³ | CD8 n°/mm³ | CD25 n°/mm³ | MHCH n°/mm³ | B n°/mm³ | NK n°/mm³ | CD14 n°/mm³ |
|---|---|---|---|---|---|---|---|---|---|---|
| 450 UI/d × 5 d | 3 ds | $T_0$ | 1521 ± 223 | 917 ± 182 | 547 ± 156 | 37 ± 30 | 156 ± 77 | 210 ± 80 | 182 ± 80 | 182 ± 75 |
| PLACEBO × 1 d | 3 ds | $T_0$ | 1615 ± 222 | 1012 ± 197 | 561 ± 162 | <12 | 183 ± 81 | 252 ± 99 | 180 ± 66 | 210 ± 81 |
| 450 UI/d × 1 d | 3 ds | $T_1$ | 1501 ± 288 | 549 ± 189 | 536 ± 141 | <11 | 180 ± 128 | 227 ± 97 | 101 ± 57 | 192 ± 79 |
| PLACEBO × 1 d | 3 ds | $T_1$ | 1637 ± 326 | 1014 ± 202 | 555 ± 188 | <12 | 191 ± 80 | 261 ± 72 | 170 ± 89 | 177 ± 63 |
| 450 UI/d × 1 d | 3 ds | $T_2$ | 1587 ± 132 | 938 ± 183 | 589 ± 97 | <11 | 175 ± 126 | 242 ± 85 | 230 ± 98 | 215 ± 72 |
| PLACEBO × 1 d | 3 ds | $T_2$ | 1723 ± 329 | 1083 ± 189 | 607 ± 172 | 34 ± 21 | 189 ± 82 | 297 ± 62 | 199 ± 71 | 206 ± 80 |
| 450 UI/d × 1 d | 3 ds | $T_3$ | 1654 ± 234 | 940 ± 184 | 631 ± 101 | 49 ± 41 | 238 ± 124 | 231 ± 91 | 176 ± 76 | 234 ± 67 |
| PLACEBO × 1 d | 3 ds | $T_3$ | 1673 ± 124 | 1045 ± 178 | 588 ± 76 | <12 | 193 ± 91 | 250 ± 49 | 202 ± 94 | 351 ± 82 | b vs a = $p < 0.01$; d vs e = $p < 0.05$; f vs e = $p < 0.01$
Student's "t" test

What is claimed is:

1. A method of treating a human having type C viral hepatitis comprising administrating to the human a daily dose of a liquid formulation of human α-interferon, wherein the daily dose is administered by a peroral route, and wherein the daily dose is between 100 and 500 IU.

2. The method of claim 1 wherein the human α-interferon is obtained from a lymphoblastoid cell culture.

3. The method of claim 1 wherein the human α-interferon is obtained from lymphocyte cells.

4. The method of claim 1 wherein the formulation is administered in a single dosage unit having a volume of approximately 1 milliliter.

5. The method of claim 2 wherein the formulation is administered in a single dosage unit having a volume of approximately 1 milliliter.

6. The method of claim 3 wherein the formulation is administered in a single dosage unit having a volume of approximately 1 milliliter.

* * * * *